US007901406B1

(12) United States Patent
Lechot (10) Patent No.: US 7,901,406 B1
(45) Date of Patent: Mar. 8, 2011

(54) CONTOURED REAMER TEETH (75) Inventor: André Lechot, Orvin (CH)

(73) Assignee: Greatbatch Medical S.A., Orvin (CH)

( * ) Notice: Subject to any disclaimer, the term of this patent is extended or adjusted under 35 U.S.C. 154(b) by 637 days.

(21) Appl. No.: 11/935,279

(22) Filed: Nov. 5, 2007

Related U.S. Application Data (63) Continuation of application No. 10/500,944, filed on Jul. 7, 2004, now Pat. No. 7,850,691.

(51) Int. Cl.
*A61B 17/00* (2006.01)
(52) U.S. Cl. .......................... 606/81; 606/86 R
(58) Field of Classification Search .............. 30/49, 352, 30/356; 83/468.8, 468.93, 853; 407/53–56, 407/58–59, 61–63; 606/79–85, 89, 91, 170, 606/176–180
See application file for complete search history.

(56) References Cited

U.S. PATENT DOCUMENTS

| | | | | |
|---|---|---|---|---|
| 4,116,200 A * | 9/1978 | Braun et al. | ..................... | 606/81 |
| 5,302,234 A * | 4/1994 | Grace et al. | ..................... | 216/47 |
| 5,968,049 A * | 10/1999 | Da Rold | ..................... | 606/80 |
| 6,001,105 A * | 12/1999 | Salyer | ..................... | 606/81 |
| D468,598 S * | 1/2003 | Mistretta | ..................... | D7/678 |
| 7,850,691 B2 * | 12/2010 | Lechot | ..................... | 606/81 |

* cited by examiner

*Primary Examiner* — Thomas C Barrett
*Assistant Examiner* — Larry E Waggle, Jr.
(74) *Attorney, Agent, or Firm* — Michael F. Scalise (57) ABSTRACT

An acetabular reamer (10') for cutting a required cut shape. The reamer has a cutting shell (12') having a series of doubly curved cutting teeth (16') thereon of a quantity to substantially reduce a cutting pressure on each tooth as well as to reduce a size of a typical chip generated upon cutting. Substantially all the teeth each have a matched arc cutting edge (20') of substantial length that has a cutting profile which substantially matches a profile of a shape to be cut. Such a configuration reduces the number of teeth required to cut the shape.

12 Claims, 8 Drawing Sheets

CONTOURED REAMER TEETH

CROSS REFERENCE TO RELATED APPLICATION

This application is a continuation application of U.S. application Ser. No. 10/500,944, now U.S. Pat. No. 7,850,691 filed Jul. 7, 2004, the content of which is incorporated herein by reference thereto.

BACKGROUND OF THE INVENTION

The invention relates to surgical products, and in particular, to surgical reamers for cutting shaped cavities in bone.

In order to produce a shaped cavity in bone for a hip implant, which requires smooth walls and accurate shape, it is advantageous that the reamer shell or cutting bowl be hemispherical. Further, the cutting teeth must be properly located and oriented. Still further, the tooth height is important to the size of bone chip and thus to the accuracy of the shape cut by the reamer.

In most cases, an implant in a hip socket is best fixed to a concave, hemispherical cavity. However, such a shape is not strictly necessary. Other acetabular cutting shells are non-hemispherical and so the principle explained here may be adapted to include such other geometries.

It is increasingly important, especially with cementless hip surgery, that the acetabulum be reamed to an exact form, generally a hemisphere, thus allowing maximal contact between the bone and the definitive (hemispherical) implant.

Further, there is increasing emphasis on cutting a smaller incision to minimize the trauma to the patient and to augment the rate of recovery. Meeting this additional requirement provides an additional challenge to the designers of medical instruments and implants. In addition, the change in surgical procedure includes the fact that the surgeon now more often maintains the acetabular reamer handle on a single axis rather than performing the step of "sweeping" the end of the tool handle through an angle and thus continuously changing the axis of the reamer cut. If a test is made maintaining a prior art reamer handle on a constant axis, then a series of concentric rings are cut that, on a macro-scale, approximate a hemisphere. When the surgeon "sweeps" the axis of the reamer handle, these irregularities are removed (in a similar manner to polishing) yielding a hemispherical surface.

In an effort to maximize the number of concentric rings, to minimize chatter/vibration and thus approach a smooth hemispherical surface without sweeping, it is desirable to add more teeth. However, when this is done, mechanical strength decreases. Further, it is more difficult in this case to insure that the cut profile of each tooth overlaps. Larger teeth have been attempted but either the chip size and cutting stresses were too large or the reamer was too complex. Further, due to the large opening adjacent the larger teeth, mechanical strength was sacrificed.

U.S. Pat. No. 5,116,165 to Sayler describes a reamer having a limited number of discrete blade-like teeth. These teeth are defined by a single curve of the profile of the form to be cut. In other words, these teeth are flat. Such a tooth form thus is not supported in that no structure is provided to help maintain the form of the tooth (other than the tooth itself) when faced with the sometimes unusually high cutting pressures of reaming. Further, the integrity of the spherical form of the reamer can be affected when there are a limited number of extensive slits of cuts in the spherical. This integrity is affected by the fact that high stresses are induced at the sharp corners of the slits.

It is often the case that the form of the tooth is a function of the original material form: the sheet material or the base diameter of the hemisphere or of the manufacturing method. Often no consideration is given to the form of the cut surface. Therefore, the cut of a single tooth often only approximates the required form of a sphere or a hemisphere. For example, it may yield a planar surface or have a radius different than that required and further generate an overall hemisphere that is irregular.

Therefore, what is needed is a reamer that minimizes the discrete cut surfaces and generates a series of cuts that comprise a single defined geometry. Further, what is needed is a tooth form that can be controlled independently of the form of the original material form.

SUMMARY OF THE INVENTION

The above problems are solved through the provision of an acetabular reamer for cutting a required cut shape, the reamer having a cutting shell on which are located a series of doubly-curved cutting teeth thereon of a quantity sufficient to substantially reduce a cutting pressure on each tooth as well as to reduce a size of a typical chip generated upon cutting. Substantially all the teeth each have a matched arc cutting edge of substantial length that has a cutting profile which substantially matches a profile of a shape to be cut. Such a configuration reduces the number of teeth required to cut the shape. Further, by punching up or forming a larger number of smaller teeth, it is easier to maintain the spherical shape of the reamer.

The invention thus gives an improved quality of cut surface and allows fewer teeth to be employed.

DETAILED DESCRIPTION OF THE PREFERRED EMBODIMENT

Figure 1:
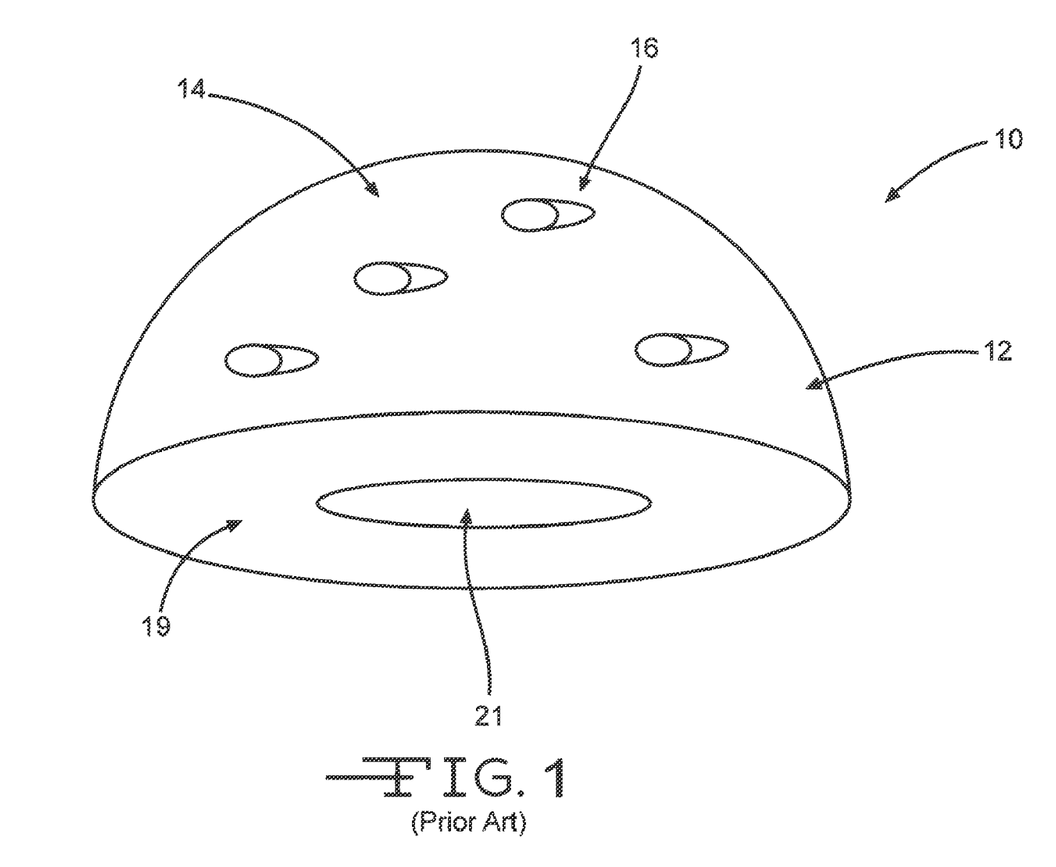
FIG. 1 is a perspective view of a reamer of the prior art.

Referring to FIG. 1, a typical acetabular reamer 10 of the prior art is shown. The reamer 10 has a cutting bowl or shell 12 defining a surface 14 on which are located teeth 16 adjacent openings 18 (FIGS. 2A to 2C). A base 19 provides a tool-engaging device (not shown) which typically engages an opening 21 therein.

Figure 2A:
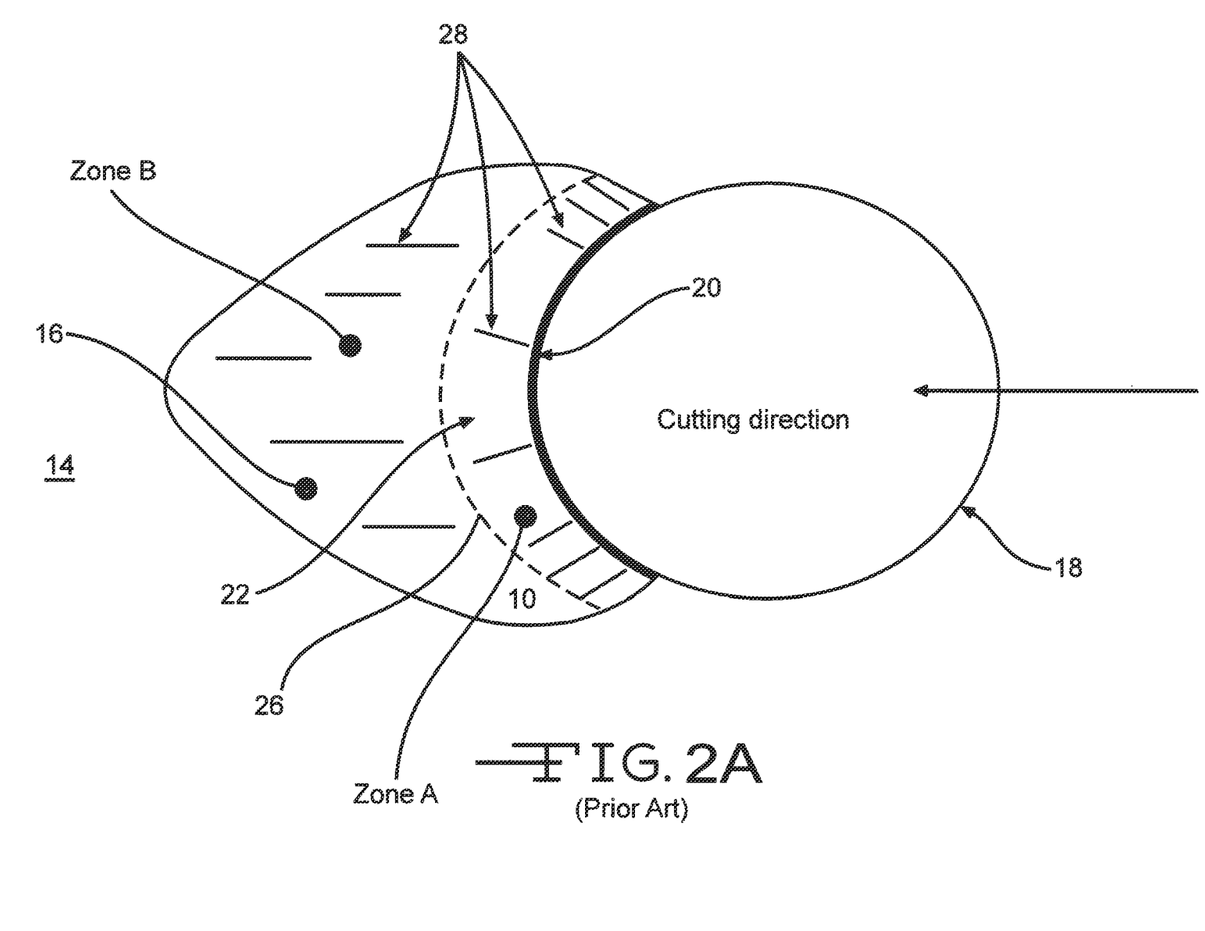
FIG. 2A is a top view of a tooth of a reamer of the prior art.

Referring now to FIG. 2A, a tooth 16 of the reamer 10 is shown. The tooth 16 has a diverging surface 22 ("rise", marked Zone A) backing up the cutting edge 20. Some distance behind the cutting edge 20 (to the left of the cutting edge in the figure), about where the dashed line 26 is located (dashed line 26' in FIG. 3A), this surface begins to curve inwardly toward the surface of Zone B, and then towards the reamer cutting bowl surface 14. Surface reflection lines 28 help indicate the form of these surfaces.

Figure 2B:
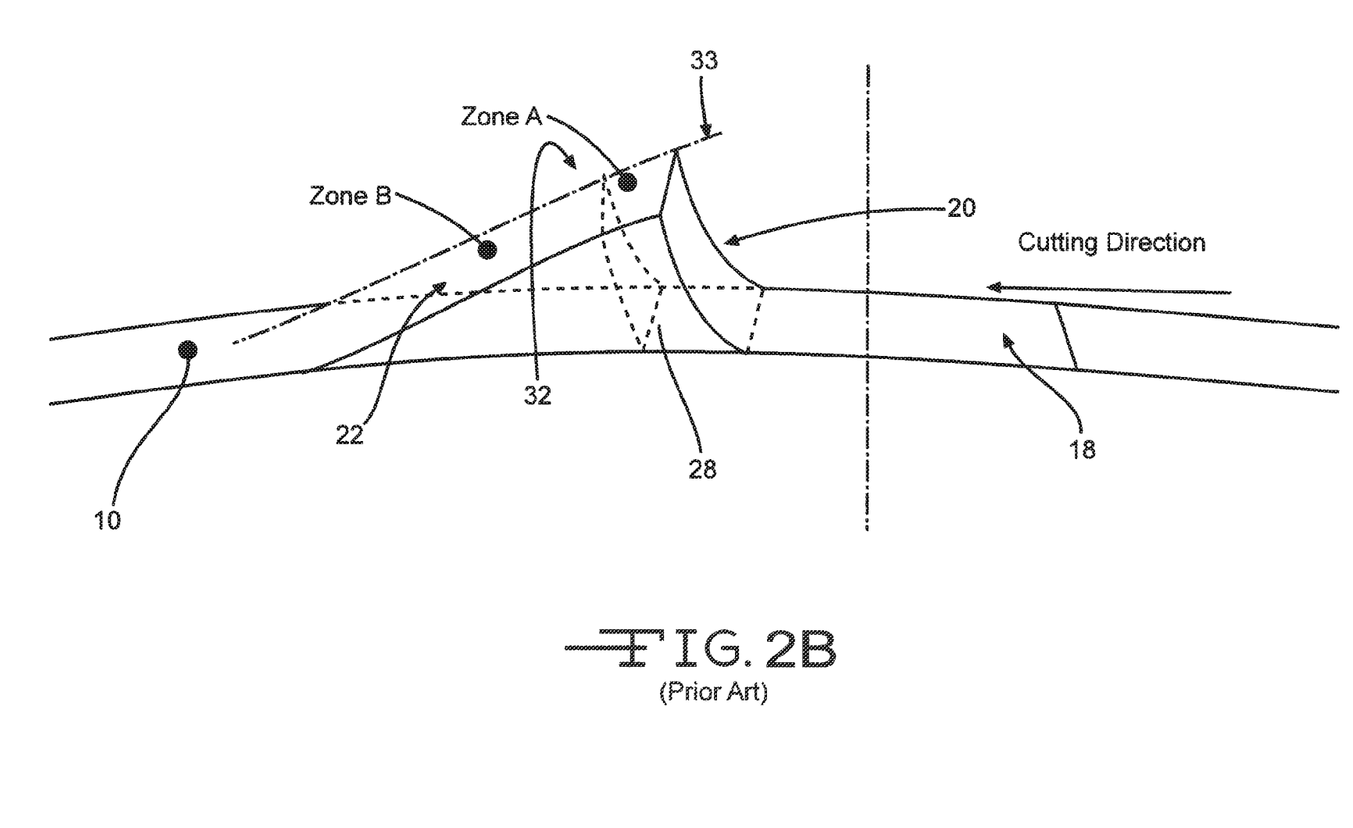
FIG. 2B is a side cross-sectional view of a tooth of a reamer of the prior art.

Referring now to FIG. 2B, a cross sectional side view of the tooth profile 32 of the prior art reamer 10 is shown. The form of the profile 32 (32' in FIG. 3B) of the rise 22 is non-linear as indicated (compare profile 32 with broken line 33).

Figure 2C:
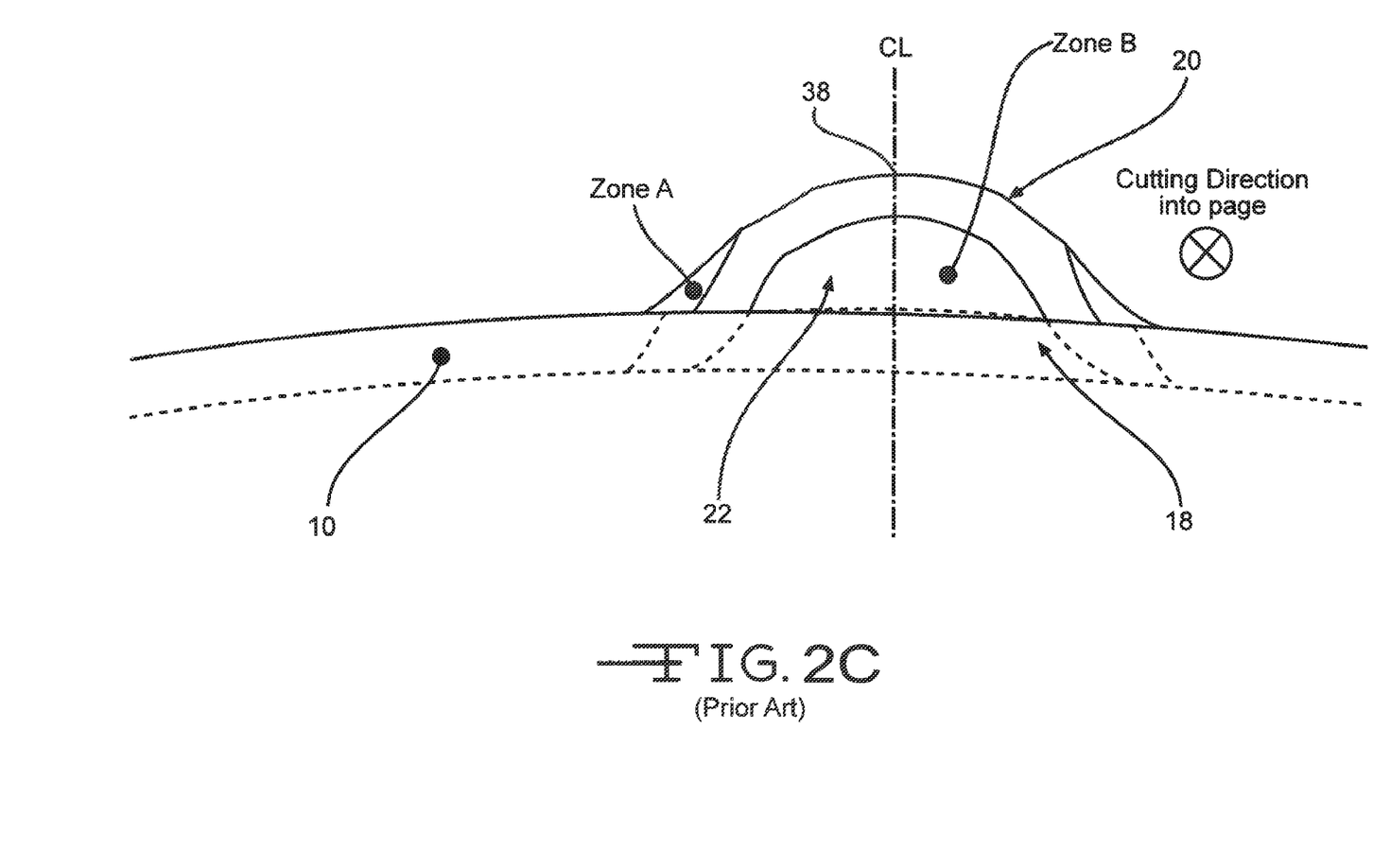
FIG. 2C is a front view of a tooth of a reamer of the prior art.

Referring to FIG. 2C, the diverging surfaces 22 of Zone A are visible when one examines a front view of the tooth 16 of the prior art reamer 10. In other prior art reamers, not shown, corresponding portions of the rise 22 are not visible in a front view but are hidden from view, due to their convergence toward an apex.

These rises 22, respective cutting edges 20, and openings 18 are either positioned on the reamer cutting surface in a spiral arrangement or randomly. The term "spiral" is meant to include any form in which the cutting teeth 16 are orderly organized in a manner to sweep out the entire shape to be cut A preferred spiral arrangement in an arrangement in which adjacent teeth are uniformly angularly offset from each other at any adjacent circle of latitude, namely, that adjacent teeth lie on differing circles of longitude evenly spaced apart from one another. Further, it is preferred that there is a given overlap between adjacent cutting rings (i.e., the rings swept out by each tooth 16).

These prior art reamers 10 have a crest 38, which generally approximates a narrow Peak. Note that FIG. 1 shows only a few representative teeth 16. Actually, due to the fact that the teeth only cut at this narrow peak 38, the entire surface of the hemisphere must be covered with many teeth 16, in order that there be sufficient cutting points to cut an approximated hemispherical surface in the bone.

Figure 3A:
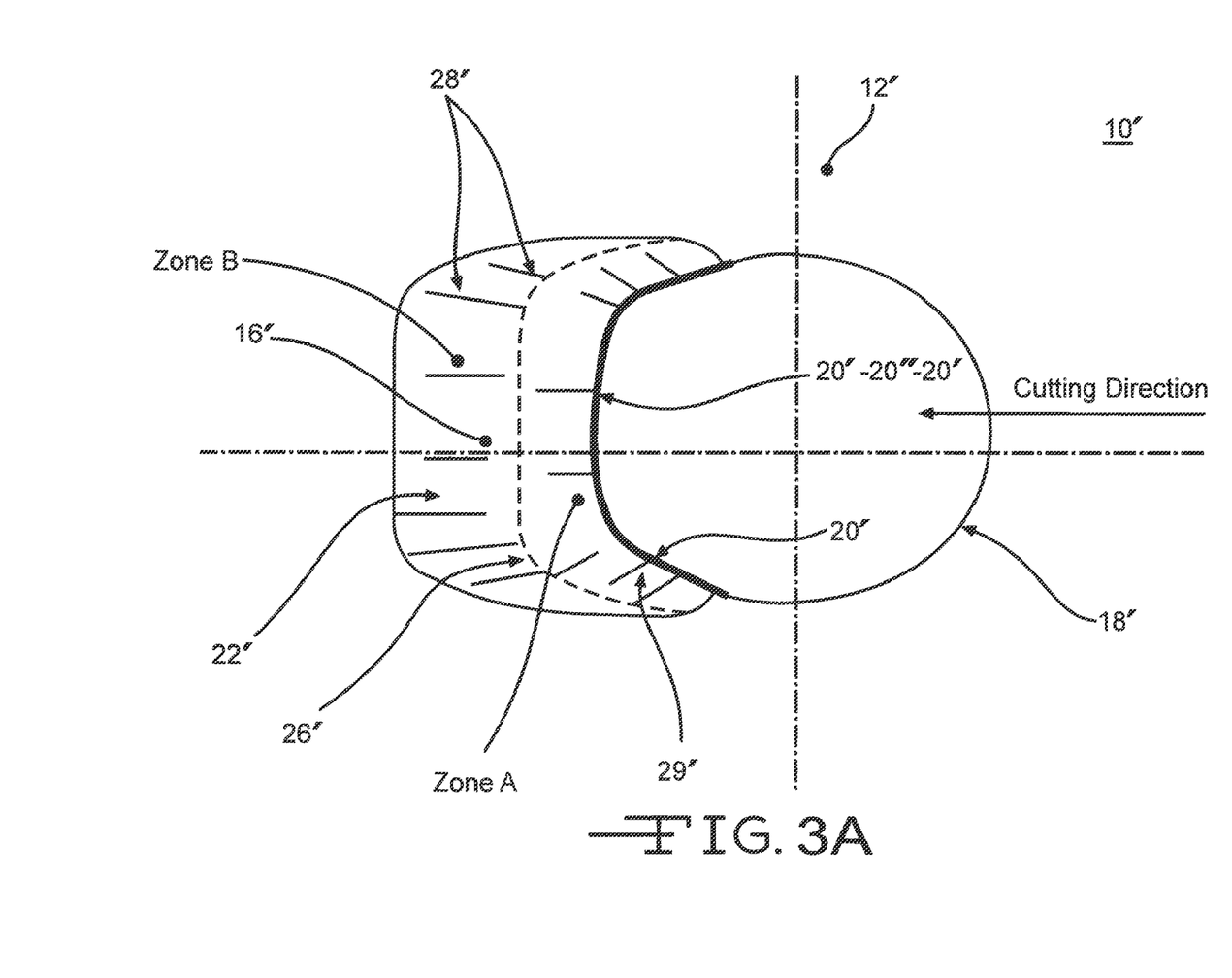
FIG. 3A is a top view of a tooth of a reamer of the invention.
Figure 3B:
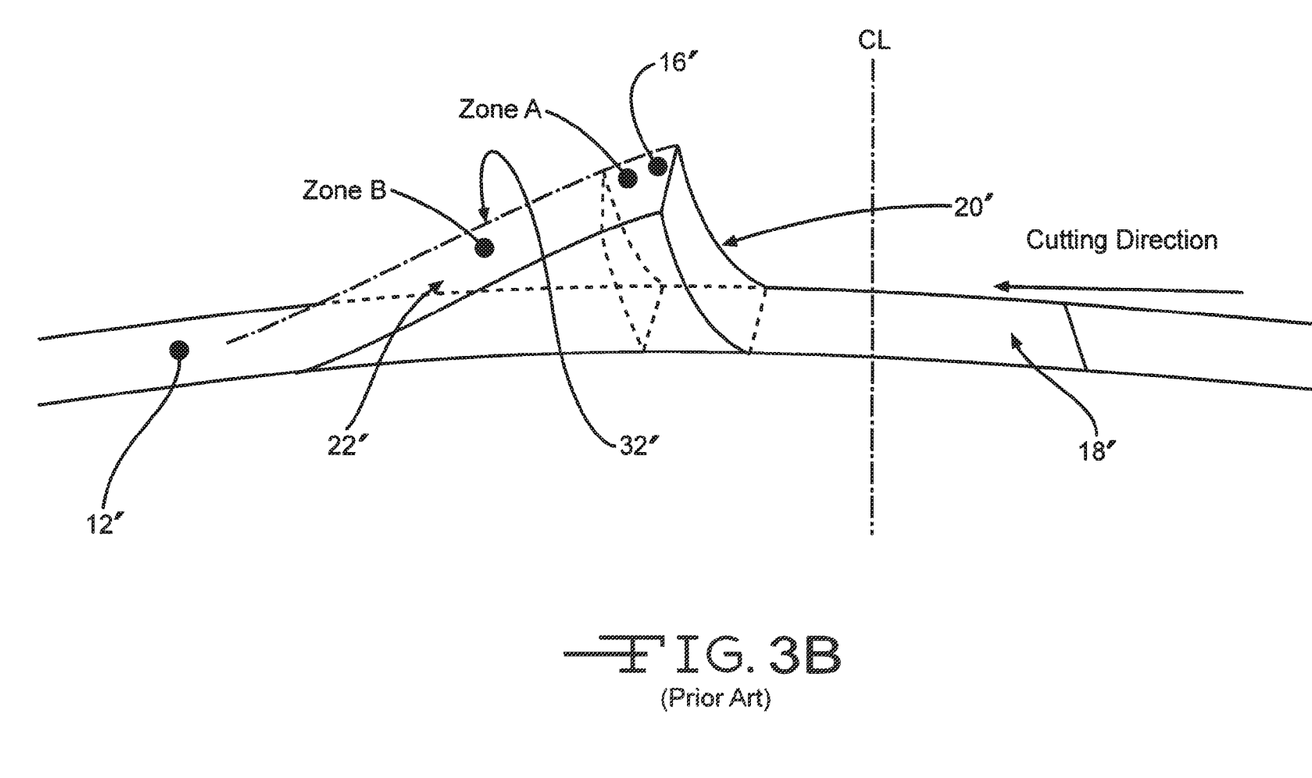
FIG. 3B is a side cross-sectional view of a tooth of a reamer of the invention.
Figure 3C:
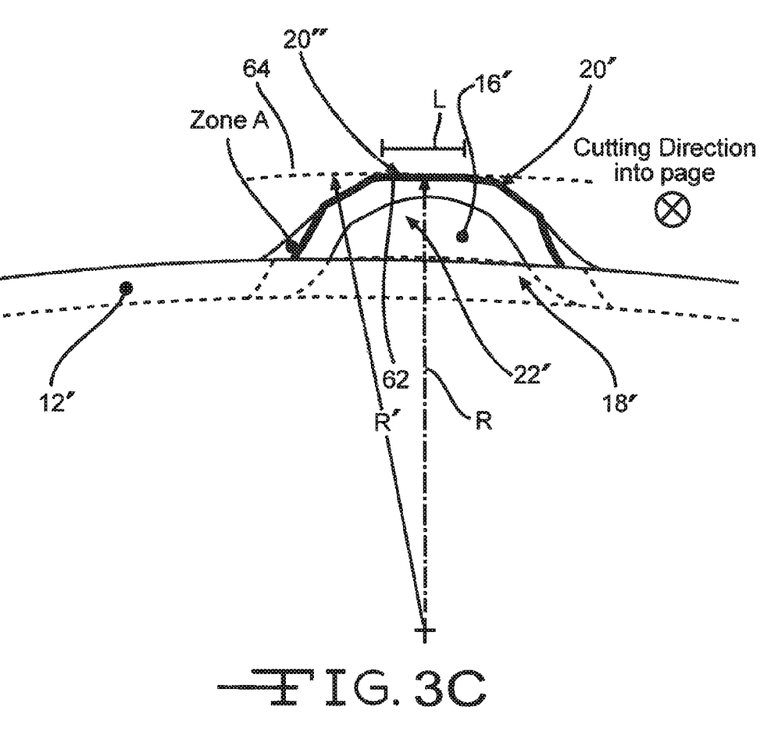
FIGS. 3C and 3D respectively are: a front view of a tooth of a reamer of the invention, and a front view of two teeth disposed in combination to make a smooth cut of a portion of the contour of the profile of the surface of the shape to be cut.
Figure 3D:
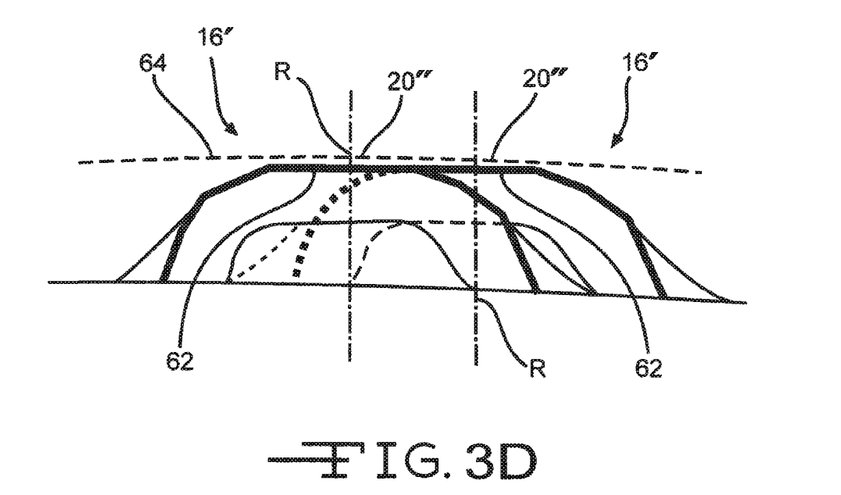

Referring now to FIGS. 3A to 3C, the present invention has a cutting shell 12' on which are located a series of doubly-curved cutting teeth 16' thereon of a quantity to substantially reduce a cutting pressure on each tooth as well as to reduce a size of a typical chip generated upon cutting. Substantially all the teeth 16' each have a matched arc cutting edge 20" of substantial length L that has a cutting profile 62 which substantially matches a profile 64 of a shape to be cut 80. The matched arc cutting edge 20" is adjacent secondary cutting edges 20' supported by adjacent rise portions 29', which may also be characterized as gusset or buttress portions, which curve back toward the cutting shell 12° and support the secondary cutting edges 20'. The overall cutting edges 20'-20"-20' are therefore doubly-curved in that at least two distinct curves (one associated with cutting edges 20' and the other associated with cutting edge 20") are required to define each cutting edge 20°-20"-20'. An opening 18' precedes the cutting edges as the reamer 10' is rotated for cutting. Because the matched arc cutting edge 20" is not a peak or point cutter, but rather a profile cutter, such a configuration reduces the number of teeth required to cut the shape. The invention thus gives an improved quality of cut surface and allows fewer teeth 16' to be employed.

Although the cutting edge 20" appears flat in the figure, its contour 62 actually follows the contour of the profile 64 of the surface of the shape to be cut 80, in this case, a hemispherical surface. In this embodiment, the radius R of the cutting edge 20" matches the radius R' of the surface to be cut.

Contrary to conventional wisdom, the new tooth 16' is not generated by making a larger or wider opening 18 adjacent to the tooth. The opening 18' is, as in the prior art, substantially round in shape. The tooth 16' is generated by the manner in which the tooth is deformed to match the profile of the eventual shape. In this embodiment, the rise 22' approximates the shape of a rectangular prism intersecting the cutting bowl at a tangent to the surface of the cutting bowl 12'. The teeth 16' have surfaces in Zone A which follow the cutting edge 20' and clearly diverge from surfaces associated with Zone B.

Further, it has been learned that by forming or punching up smaller teeth, it is easier to ensure that the spherical shape of the reamer is not compromised.

Figure 4:
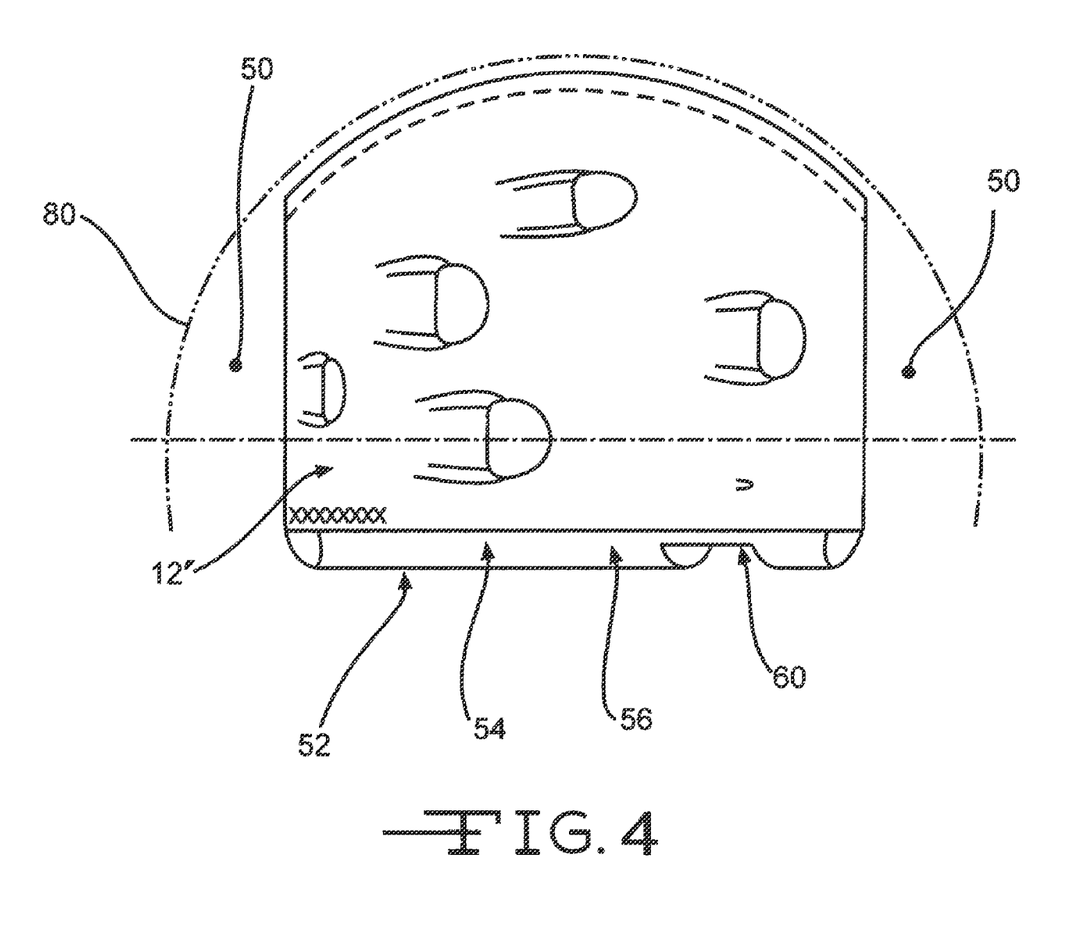
FIG. 4 is a side view of the reamer of the invention.
Common reference numerals are used for the same or analogous features throughout the drawings.

For any given radius from the center of the acetabulum to the periphery, a different part of the sector is cut by a different tooth 16'. The invention of a longer tooth 16' following the rounded opening 18' and which matches more closely the required radius R, means that a reduced number of teeth are required to cut the full radius. Further, the use of a series of cutting teeth 16' on the cutting shell 12' substantially reduces the cutting pressure on each tooth as well as reduces a size of a typical chip generated upon cutting. The ability to use fewer teeth 16' further allows sections 50 (shown in FIG. 5) of the hemisphere to be removed while maintaining a high quality of cut surface. An example of an acetabular reamer with sections cut away is given in the diagrams of PCT applications serial numbers PCI/IB01/02675 and PCI/IB01/02676 entitled HOLDER FOR A SURGICAL REAMER and SURGICAL REAMER, respectively, filed on 21 Dec. 2001, the contents of which are incorporated herein by reference thereto.

The present invention generates a tooth 16' with a wider cutting path that is therefore easier to overlap with the cut generated by the next tooth at a different latitudinal elevation on the hemisphere. Additionally the tooth 16' cuts a sector of the required hemisphere, matching the required radius exactly. Consequently, as already mentioned, the improved tooth allows a full hemisphere to be cut with fewer teeth.

Preferably, the reamer 10' includes a series of cutting teeth 16' arranged uniformly and spaced apart on the cutting shell. These teeth 16' may be arranged in a spiral arrangement on the cutting shell 12'.

In an alternate embodiment, best seen in FIG. 4, the cutting shell is a portion of a hemisphere, in this case, in which sections 50 (shown by dashed lines) have been removed in the manufacturing process. In this embodiment, the length of the cutting edges are selected so as to completely cut the shape while being of a number that still ensures good mechanical strength. The longer cutting edges allows the use of less teeth while still cutting a good hemispherical form than permissible with a cutting shell that has a more complete hemispherical shape.

A tool engaging portion 52 is comprised of two intersecting bars 54 and 56, one bar 54 of which optionally having two flats 60 (only one of which is shown) on its outer ends, adjacent their connecting points on the reamer cutting shell 12'.

In an advantage, the reamer of the invention minimizes the discrete cut surfaces and generates a series of cuts that comprise a single defined geometry.

In another advantage, the form of the tooth is no longer necessarily dependent for its form to that of the original material on which the tooth is itself formed.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A reamer, which comprises:
   a) a cutting shell defining a spherical center and having a shell curvature comprising at least a portion of a first hemisphere extending from an apex to a lower edge, the cutting shell being rotatable about a longitudinal axis; and
   b) a plurality of cutting teeth thereon, wherein at least one of the cutting teeth comprises two buttress portions extending from the cutting shell and meeting an intermediate cutting edge curvature as a line segment of a second hemisphere, wherein the line segment comprises a continuum of cutting edge radii, each radii originating at the spherical center with the second hemisphere being greater than the first hemisphere of the cutting shell and wherein the plurality of cutting teeth are rotatable about the longitudinal axis.

2. The reamer of claim 1 wherein a generally circular hole precedes each cutting tooth as the reamer is rotated for cutting.

3. The reamer of claim 1 wherein the cutting teeth are arranged uniformly and spaced apart on the cutting shell.

4. The reamer of claim 1 wherein the cutting teeth are arranged in a spiral arrangement on the cutting shell.

5. A reamer, which comprises:
   a) a cutting shell that is rotatable about a longitudinal axis, wherein the cutting shell extends from an apex to a lower edge and has a curvature defined by a plurality of cutting shell radii of the same length extending from a focal point located on the longitudinal axis; and
   b) a plurality of cutting teeth thereon, wherein at least one of the cutting teeth comprises two buttress portions extending from the cutting shell and meeting an intermediate cutting edge spaced furthest from the cutting shell, the cutting edge being continuously defined from one buttress to the other buttress by a continuum of cutting edge radii of the same length with each radii extending from the same focal point as the plurality of cutting shell radii.

6. The reamer of claim 5 wherein a generally circular hole precedes each of the cutting teeth as the reamer is rotated for cutting.

7. The reamer of claim 5 wherein the cutting teeth are arranged uniformly and spaced apart on the cutting shell.

8. The reamer of claim 5 wherein the cutting teeth are arranged in a spiral configuration on the cutting shell.

9. A reamer, which comprises:
   a) a cutting shell defining a spherical center and having a shell curvature comprising at least a portion of a first hemisphere extending from an apex to a lower edge, the cutting shell being rotatable about a longitudinal axis; and
   b) a plurality of cutting teeth thereon, wherein at least one of the cutting teeth comprises a cutting edge having a curvature as a line segment of a second hemisphere, wherein the line segment comprises a continuum of cutting edge radii, each radii originating at the spherical center with the second hemisphere being greater than the first hemisphere of the cutting shell and wherein the plurality of cutting teeth are rotatable about the longitudinal axis.

10. The reamer of claim 9 wherein a generally circular hole precedes each of the cutting teeth as the reamer is rotated for cutting.

11. The reamer of claim 9 wherein the cutting teeth are arranged uniformly and spaced apart on the cutting shell.

12. The reamer of claim 9 wherein the cutting teeth are arranged in a spiral configuration on the cutting shell.

* * * * *